United States Patent [19]

Lemar et al.

[11] Patent Number: 6,096,508
[45] Date of Patent: Aug. 1, 2000

[54] METHOD OF REDUCING BACKGROUND IN BIOTIN-BASED ASSAYS

[75] Inventors: Michael S. Lemar, Gaithersburg; Katherine MacLean Peterson, Elkridge; Carrington S. Cobbs, Ellicott City, all of Md.

[73] Assignee: Kirkegaard & Perry Laboratoies, Inc., Gaithersburg, Md.

[21] Appl. No.: 08/515,932

[22] Filed: Aug. 16, 1995

[51] Int. Cl.$^7$ .................... G01N 33/53; G01N 33/543; G01N 33/544; C12Q 1/68

[52] U.S. Cl. ................ 435/7.5; 435/6; 435/7.1; 435/7.95; 435/962; 436/518; 436/528; 436/531; 436/825; 436/826

[58] Field of Search ................ 435/6, 7.1, 7.5, 435/7.95, 962; 436/518, 528, 531, 825, 826

[56] References Cited

U.S. PATENT DOCUMENTS

| | | | |
|---|---|---|---|
| 3,654,090 | 4/1972 | Schuurs et al. | 435/28 |
| 3,839,153 | 10/1974 | Schuurs et al. | 435/7.93 |
| 4,016,043 | 4/1977 | Schuurs et al. | 435/5 |
| 4,152,411 | 5/1979 | Schall, Jr. | 424/1 |
| 4,334,017 | 6/1982 | Plotkin et al. | 435/7.9 |
| 4,684,609 | 8/1987 | Hsu | 435/7.9 |
| 4,746,604 | 5/1988 | Mowshowitz | 435/7.1 |
| 4,889,798 | 12/1989 | Rabbani | 435/6 |
| 4,894,325 | 1/1990 | Eaglehardt et al. | 435/6 |
| 4,994,373 | 2/1991 | Stavrianopoulos et al. | 435/6 |
| 5,028,525 | 7/1991 | Gray et al. | 435/6 |
| 5,252,466 | 10/1993 | Cronan, Jr. et al. | 435/69.7 |
| 5,255,325 | 10/1993 | Miller et al. | 435/6 |
| 5,262,334 | 11/1993 | Berenson et al. | 436/541 |
| 5,281,521 | 1/1994 | Trojanowski et al. | 435/7.5 |
| 5,332,679 | 7/1994 | Simons et al. | 436/518 |
| 5,413,906 | 5/1995 | Eberle et al. | 435/5 |
| 5,482,698 | 1/1996 | Griffiths | 424/141 |
| 5,487,975 | 1/1996 | Miller et al. | 435/7.5 |

OTHER PUBLICATIONS

Duhamel et al., "Prevention of Nonspecific Binding of Avidin," *Methods In Enzymology*, 184:201–207 Academic Press Inc., 1990.

Woods et al., "Suppression of Endogenous Avidin Bending Activity in Tissues and Its Relevance to Biotin–Avidin Detection Systems," J. Histochem. Cytochem. 29(10):1196–1204, 1981.

International Search Report of PCT/US96/13046 dated Jul. 08, 1997.

Box V of the Written Opinion Dated Jun. 30, 1997 for PCT/US96/13046.

*Annals of Clinical and Lab. Sci*, 24(4):324–338 (1994)(with Abstract also) Szakacs et al.

Hofmann et al., "Avidin Binding of Carboxyl–Substituted Biotin and Analogues", *Biochemistry* 21:978–984 (1982).

Mock et al., "A Study of the Interaction of Avidin with 2–Anilinonaphthalene–6–Sulfonic Acid as a Probe of the Biotin Binding Site", *Biochimico et Biophysica Acta* 956:23–29 (1988).

Clark et al., "Suppression of Nonspecific Binding of Avidin–Biotin Complex (ABC) to Proteins Electroblotted to Nitrocellulose Paper", *J. Histochemistry and Cytochemistry* 34(11):1509–1512 (1986).

International Search Report of PCT/US96/13046 dated Oct. 24, 1996.

Hsu, Su–Ming, "Immunoperoxidase Techniques Using the Avidin–Biotin System", *In: Enzyme–Mediated Immunoassay*, 1985, pp. 467–476.

*Primary Examiner*—James C. Housel
*Assistant Examiner*—Gailene R. Gabel
*Attorney, Agent, or Firm*—Banner & Witcoff Ltd.

[57] ABSTRACT

This invention relates to an improvement in a method for detecting labeled molecules and especially biotinylated molecules and particularly relates to a method for reducing background signal problems in such detection methods.

10 Claims, 5 Drawing Sheets

(a) (b) (c) (d) (e) (f) (g) (h) (i) (j) (k)

(a) (b) (c) (d) (e) (f) (g) (h)

METHOD OF REDUCING BACKGROUND IN BIOTIN-BASED ASSAYS

BACKGROUND OF THE INVENTION

1. Field of the Invention

This invention relates to an improvement in methods for detecting labeled molecules and especially biotinylated molecules. More particularly, the invention relates to an improvement in detection systems based on the interaction between biotin and either avidin or streptavidin.

2. Description of Related Art

The analysis and detection of minute quantities of substances in biological and nonbiological samples has become a routine practice in clinical, diagnostic and analytical laboratories. These detection techniques can be divided into two major classes: (1) those based on ligand-receptor interactions (e.g., immunoassay-based techniques), and (2) those based on nucleic acid hybridization (e.g., polynucleotide sequence-based techniques). Immunoassay-based techniques are characterized by a sequence of steps comprising the non-covalent binding of an antibody and an antigen complementary to it. Polynucleotide sequence-based detection techniques are characterized by a sequence of steps comprising the non-covalent binding of a labeled polynucleotide sequence or probe to a complementary sequence of the analyte under hybridization conditions in accordance with the Watson-Crick base pairing of adenine and thymine, and guanine and cytosine, and the detection of that hybridization.

In both classes of detection techniques, a nucleic acid probe or a polypeptide probe can be modified by a heterologous moiety and the heterologous moiety can be detected through a signaling moiety. The heterologous moiety contains at least two complex forming sites that form two different complexes, i.e., two kinds of complexes can be formed. The first complex forming site is utilized to attach the heterologous moiety to the probe (e.g., the polynucleotide or polypeptide) and the second (and additional) complex forming site(s) is(are) utilized to recognize (e.g., bind to) or activate the signaling moiety, with each complex formed being different and not interfering with each other. The signaling moiety contains a complex forming site that recognizes (e.g., binds to) the second complex forming site(s) of the heterologous moiety and a signaling site or portion that is capable of generating a signal directly or indirectly. The signal thus can be used to demonstrate the successful binding of the signaling moiety to the heterologous moiety.

An example of a nucleic acid probe or a polypeptide probe modified by a heterologous moiety is a biotinylated nucleic acid or a biotinylated polypeptide probe. Signaling moieties that are capable of creating a signal encompass a vast number of signal generating systems, including a moiety which generates a signal itself, e.g., a dye, a radioactive molecule, a chemiluminescent material, a fluorescent material or a phosphorescent material, or a moiety which upon further reaction or manipulation will give rise to a signal, e.g., a enzyme-linked system using an enzyme such as catalase, peroxidase, β-glucuronidase, β-D-glucosidase, β-D-galactosidase, urease, glucose oxidase, galactose oxidase, or alkaline phosphatase. Substrates for such enzymes are well known and may produce a chromogenic, fluorescent or chemiluminescent signal for example. An example of a signaling moiety that has been utilized to detect a biotinylated probe is a modified avidin or streptavidin, normally modified by conjugation with an enzyme, such as horseradish peroxidase or alkaline phosphatase.

The identification and detection of biotinylated molecules attached to a target material in a sample immobilized on a solid phase support, such as a filter membrane, has generally been plagued by a background signal problem. The signaling moiety is localized on the solid support or solid phase and activated for reasons other than the presence of the target material. Nonspecific signal can occur under conditions wherein a labeled detector probe or a signaling moiety, such as a streptavidin-enzyme conjugate, indiscriminately binds for example (i) to the solid support or solid phase, such as a filter membrane, on which an assay is being conducted, or (ii) to a substance, usually a protein, used to block the solid phase. This localization of the labeled detector probe or signaling moiety for reasons other than the identification or recognition of a target material is often times referred to as non-specific binding. The consequence of such non-specific binding may be an inability to differentiate the desired signal from background noise.

Researchers have compensated for the variability in a solid phase membrane's propensity to bind the detector molecule or probe and/or the signaling moiety, e.g., enzyme-conjugated streptavidin, by treatments such as the use of heterologous DNA, an extended blocking step or a high salt washing step prior to addition of the indicator substrate (in this regard, see, R. K. Clark, et al., *The Journal of Histochemistry and Cytochemistry,* 34(11):1509–1515 (1986)). These steps have yielded various degrees of success, dependent to a large extent on the properties of the membrane itself, but improvements are still being sought. Nylon membranes, in particular, have continued to be a problem. Nylon membranes are used routinely by molecular biologists and have been the membrane of choice for nucleic acid work. Nucleic acids are readily immobilized on nylon membranes via UV irradiation. Nylon membranes also are very hardy and hold up well to multiple reprobing cycles involving high temperatures and chemical denaturants. Unfortunately nylon membranes generally exhibit considerable vendor-to-vendor, as well as lot-to-lot variability in the incidence of background signal problems, when used as a solid support, such as for nucleic acid hybridization assays, and particularly when used in conjunction with modified avidin and streptavidin as the signaling moiety.

It is therefore an object of this invention to provide a novel method of reducing background interference in ligand-receptor and nucleic acid hybridization-based assays and especially in such assays which rely on the biotin-avidin/streptavidin interaction for detection. The present invention is most particularly directed to nucleic acid hybridization assays which use biotinylated nucleic acid probes in connection with nylon solid phase supports.

DETAILED DESCRIPTION OF THE INVENTION

Figure 1A:
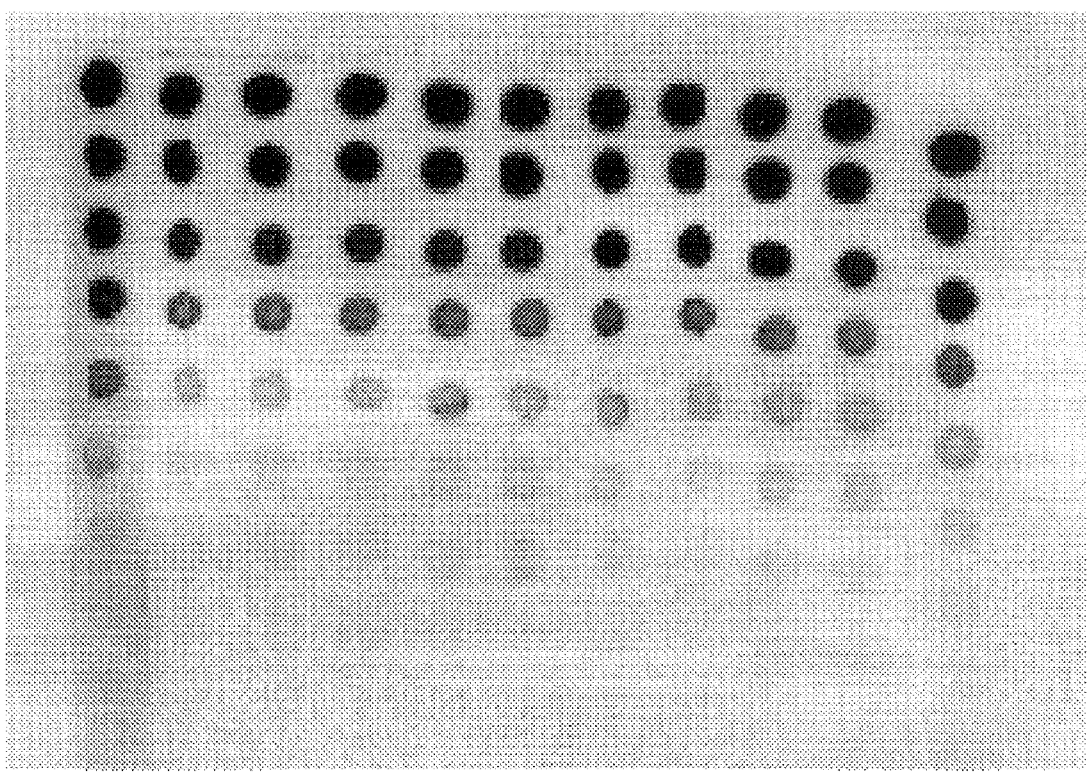
FIGS. 1*a* and 1*b* are X-ray films of a dot blot assay which show the effect of adding free biotin to a standard wash solution when conducting a nucleic acid assay respectively on PALL BIODYNE® (FIG. 1*a*) and MSI MAGNAGRAPH® (FIG. 1*b*) nylon membranes.

The present invention is directed to an improvement in assays based on the interaction of a signaling moiety with a heterologous moiety attached to a detector molecule or probe. In particular, the present invention is based on the discovery that the level of undesired background signal in such assays can be reduced by including in a wash solution used to remove excess signaling moiety (particularly including non-specifically bound signaling moiety) from the solid phase, a background signal-reducing amount of free heterologous moiety. In the broad practice of the present invention, the free heterologous moiety need not be the same moiety that is attached to the detector molecule or probe. Rather, the free heterologous moiety simply must be one that exhibits an interaction with the signaling moiety similar to that exhibited between the signaling moiety and the heterologus moiety attached to the detector molecule.

The wash step typically follows one or more of the steps of (i) sample immobilization on a solid phase, (ii) blocking the solid phase, as needed, to prevent non-specific binding of detector molecule or probe, (iii) contacting the sample with detector molecule or probe, (iv) washing the solid phase, including the sample, to remove excess (including non-specifically bound) detector molecule or probe, (v) blocking the solid phase to prevent non-specific binding of signaling moiety, and (vi) contacting the sample with signaling moiety to identify the presence of any detector molecule or probe bound to a target material in the sample. The present invention is particularly based on the surprising discovery that by including a background signal-reducing amount of free biotin in a standard wash solution in an assay based on the biotin and avidin or biotin and streptavidin interaction, i.e., an assay which uses biotin as the heterologous moiety and a modified avidin (e.g., an avidin-enzyme conjugate) or a modified streptavidin (e.g., a streptavidin-enzyme conjugate) as the signaling moiety, one can greatly reduce non-specific binding of the signaling moiety to sites other than the desired target. Thus, one can reduce the level of undesired background signal, with minimal effect on the specific signal resulting from desired binding of the signaling moiety to those biotin-labeled detector molecules or probes which are bound to the target. In those cases where the signaling moiety includes an enzyme, the wash step then is followed by contacting the sample with an indicator substrate for the enzyme.

Though not wishing to be limited to any particular technical explanation, applicants believe that free heterologous moiety, e.g., free biotin, in the wash solution preferentially binds to non-specifically bound signaling moiety, e.g., modified-avidin or modified-streptavidin, such as enzyme conjugates of avidin and streptavidin (i.e., signaling moiety not bound to the desired target), and preferentially enhances the removal of non-specifically bound signaling moiety prior to the detection and/or identification step.

The present invention, therefore, is broadly directed to all assays based on (1) ligand-receptor interactions and (2) nucleic acid hybridizations wherein a heterologous moiety is attached to a detector molecule (the detector molecule itself thereafter being selectively attached or bound to a target molecule during the assay) and the presence of a detector molecule in a test sample is indicated by an interaction between the heterologous moiety and a signaling moiety. The present invention is specifically directed to an improvement in such assays, wherein a wash step, designed to remove non-specifically bound signaling moiety from the test sample at some point during the assay is carried out with a wash solution containing an effective amount of a free heterologous moiety.

As used herein, the terms "nucleic acid", "polynucleotide" and the like are intended to refer not only to the natural polymers of ribonucleic acid (RNA) and deoxyribonucleic acid (DNA), based on the bases adenine (A), guanine (G), cytosine (C), thymine (T) and uracil (U), but also derivatives, analogs and synthetic versions thereof, incorporating or comprising synthetic, non-natural or altered nucleotides which exhibit a similar behavior in hybridization assays. In this regard, see Egholm, et al., *J. Amer. Chem Soc.*, 114 (1992):1895–1897 entitled Oligonucleotide Analogues with an Achiral Peptide Backbone. Included within this definition are inosine-substituted polynucleotides.

The term "wash solution" is intended to encompass not only true solutions but also washing compositions that may contain ingredients that are readily suspended or are considered to exist in a colloidal form at the time of use.

The terms "bound", "complexed", "attached" and words of similar import are intended to include both covalent and non-covalent interactions, which may be direct or indirect, between two moieties or molecules. An indirect bond or interaction is one where one moiety is attached to another moiety through an intermediate moiety.

The terms "free heterologous moiety" and "free biotin" mean that their complex-forming sites are not bound to a molecule, or to a binding site thereon, which they recognize.

The term "target material" refers to a moiety, such as a molecule of a denatured DNA, a protein or other material, whose presence in a sample is to be detected and/or identified. In this regard, typical samples include blood, urine, other bodily fluids, biological tissue or cells.

In one preferred embodiment, the present invention is especially directed to an improvement in nucleic acid hybridizations. According to this preferred embodiment, a biotinylated polynucleotide probe is used as a detector molecule to identify the presence of a target polynucleotide in a sample. The presence of any detector molecules or probes bound to the target polynucleotide thereafter is recognized by a streptavidin- or avidin-enzyme complex used as a signaling moiety. The improvement of the present invention centers on employing as a wash solution a composition containing an effective, non-specifically bound, signaling moiety-reducing amount of free biotin to remove any streptavidin- or avidin-enzyme complex, not specifically bound to the biotin-label on detector molecules bound to the target polynucleotide.

The binding of avidin and streptavidin to biotin is one of the most avid bonds in nature. The strength of this bond gives detection systems based on the biotin/avidin and biotin/streptavidin interaction many advantages. Researchers in the biomedical field have long utilized modified streptavidin as detection intermediates (signaling moieties) in solid phase assays wherein a specific probe has been modified with biotin. In these assays, biotin has been chemically or enzymatically coupled to probe biomolecules in ways to minimize interference with target recognition. The most common application involves biotinylated nucleic acid probes used in solid phase assays wherein the target DNA or RNA samples are immobilized, for example, on a solid support such as nitrocellulose or nylon membranes. The specific probes are placed in contact with the sample, potentially containing the target sequence(s), and are allowed to hybridize. In some cases, the solid support containing the sample may first be treated with a heterologous, denatured DNA or with a protein, such as milk protein, to block non-specific hybridization of labeled probes. See Maniatis et al., *Molecular Cloning: A Laboratory Manual, 2nd Edition*, (1988), Cold Spring Harbor Laboratory Press, Cold Spring Harbor. The sample thereafter is washed to remove non-hybridized detector molecules or probes. The detection or recognition portion of the assay then utilizes a streptavidin-enzyme conjugate which seeks out bound probe. Oftentimes, the solid phase membrane is previously treated with a blocking agent, such as a milk-based protein, intended to reduce non-specific binding of the conjugate. Following a second wash step designed to remove non-specifically bound signaling moiety, such as a streptavidin-enzyme conjugate, a substrate then is added and, to the extent any signaling moiety remains, a chromogenic, a fluorogenic or a chemiluminescent reaction product is produced.

A very similar assay is carried out wherein proteins, separated by size, are immobilized on or in a solid support. Biotinylated antibodies then serve as the specific probes or detector molecules that identify the presence of specific proteins. The subsequent steps, which generally mimic the sequence described above for a polynucleotide assay, produce a specific signal on or in the solid support.

Biotin-based detection systems commonly use alkaline phosphatase or horseradish peroxidase as the enzyme conjugated to streptavidin or avidin as the signaling moiety to detect biotin-labeled detector molecules such as DNA probes or biotin-labeled antibodies. A standard protocol for use of enzyme-conjugated streptavidin and avidin includes removal of non-hybridized probe (the first wash step) and a blocking step with excess protein before adding the enzyme-conjugated streptavidin or avidin to a blot. Subsequently, the blot will be washed (the second wash step referred to above) with a standard wash solution to remove any enzyme-conjugated streptavidin or avidin not specifically bound to a biotin-labeled probe or antibody. Thereafter, a substrate is added to produce a chromogenic, a fluorogenic or a chemiluminescent reaction with bound enzyme. Suitable substrates for alkaline phosphatase and horseradish peroxidase include 1,2-dioxetanes, 5-bromo-4-chloro-3-indolyl-phosphate/nitroblue tetrazolium, enhanced luminol or 3,3', 5,5'-tetramethylbenzidine.

As noted above, one problem with the biotin-based assays, particularly prevalent when using a nylon membrane as the solid phase, is non-specific binding of the enzyme-conjugated streptavidin or avidin to the solid phase that is not removed completely by the second wash step. This non-specific binding causes a serious background signal problem when the target sample, localized on the solid phase support, is subsequently contacted with the signal substrate. According to the novel method of the present invention, adding an effective amount of free biotin to the standard post-signaling moiety treatment wash solution, i.e. the solution of the second wash step, dramatically reduces the level of non-specifically bound enzyme-conjugated streptavidin or avidin. This significantly reduces the level of the background signal, and thus significantly increases the signal to noise ratio of the assay.

One suitable standard wash solution is an aqueous solution buffered with imidazole to a pH of about 7.0, containing a surfactant in an amount of about 0.02%, such as TWEEN® 20 surfactant, sodium chloride in an amount of about 0.16M, and ethylene diamine tetra acetic acid (EDTA) in an amount of about 0.5 mM. Those skilled in the art recoginze the wide variety of surfactants and buffers that can be used to prepare such standard wash solutions. Biotin is added to such standard wash solutions in an effective amount to remove non-specifically bound streptavidin. The appropriate amount of free heterologous moiety, such as biotin, to add to the standard wash solution to ameliorate the problem of non-specifically bound signaling moiety is a function of many factors, the optimization of which in any given assay is routine for those skilled in the art. In particular, the level of free heterologous moiety will be influenced by the length or duration of the wash step (longer washes generally requiring a lower concentration), the volume of the wash solution used (higher volumes generally requiring a lower concentration), the quantity of signaling moiety used in the identification/recognition step (larger excesses of signaling moiety generally requiring a higher concentration) and the like. The desired concentration may also be influenced by the temperature and pH of the wash step, although typically to a lesser extent. Again, a suitable optimization of these many variables is routine for those skilled in this art. Generally, biotin will be included in the wash solution in an amount between about 10 ng/ml to about 10 µg/ml. Biotin is generally employed in its natural d-sterioisomeric form, i.e., d-biotin. The present invention is applicable not only to biotin per se, but also biotin analogs and derivatives. Biotin derivatives would include biotin methyl ester and other alkyl esters. Biotin analogs would include biotin sulfone, 2'-thiobiotin, 2'-iminobiotin, d-desthiobiotin, dl-desthiobiotin, dl-desthiobiotin methyl ester and other imidazolidone derivatives. In this regard, please see Green, N. M., (1975) in *Advances in Protein Chemistry* (Anson, M. L. and Edsell, J. T., Eds), Vol. 29, pp. 85–133, Academic Press, New York.

Under the broad practice of the present invention, this method can be applied when the target DNA, RNA, or protein sample is immobilized on a variety of solid phase membrane supports including nitrocellulose, polyvinylidene fluoride (PVDF), nylon, and other materials known in the art. The invention also is applicable to tissue-based (histological) assays.

The method also is applicable to a wide variety of assay approaches as noted above, including Southern, Northern and Western blot procedures and in situ protocols, all of which include a step to remove non-specifically bound signaling moiety using a wash solution.

The invention is specifically applicable to biotin-based detection systems using a wide variety of streptavidin-modified and avidin-modified signaling moieties, including streptavdin-enzyme conjugates or avidin-enzyme conjugates in addition to horseradish peroxidase conjugates. Techniques for preparing such modified streptavidin and modified avidin are known to those skilled in the art. Suitable enzymes for making conjugates with avidin and streptavidin include (i) horseradish peroxidase for which suitable chromogenic substrates include 3,3'diaminobenzidine; 4-chloro-1-naphthol; 3-amino-9-ethylcarbazole and 3,3',5,5'-tetramethylbenzidine, suitable fluorogenic substrate include homovanillic acid and 4-hydroxy-3-methoxyphenylacetic acid, and a suitable chemiluminescent substrate includes enhanced luminol, (ii) alkaline phosphatase for which a suitable chromogenic substrate is 5-bromo-4-chloro-3-indolyl-phosphate/nitroblue tetrazolium, a suitable fluorogenic substrate is 4-methylumbelliferyl phosphate or other umbelliferyl phosphates such as 4-carboxy-umbelliferyl phosphate and its alkyl esters and a suitable chemiluminescent substrate is 1,2-dioxetane, and (iii) beta-galactosidase for which a suitable chromogenic substrate is 5-bromo-4-chloro-3-indolyl-D-galactosidase, and a fluorogenic substrate is 4-methylurnbelliferyl-beta-D-galactoside. Techniques for preparing such enzyme-labeled signaling moieties and particularly streptavidin- and avidin-enzyme conjugates is well understood by those skilled in the art.

In addition to enzyme-conjugated signaling moieties, which represent an indirect method for recognizing the presence of a detector molecule, the present invention also is directed to the use of signaling moieties that provide a direct signal for detection and/or identification. In this regard, the following signaling moieties can be mentioned, streptavidin or avidin modified with a fluorophore such as fluorescein, phycoerythrin or tetramethyl rhodamine, (useful in immunohistological and in situ hybridization applications), streptavidin modified with a colloidal moiety such as colloidal gold or a carbon sol (designed to provide a directly recognizable visual signal) and streptavidin modified with a radioisotope such as $^{125}$I. As used herein, the terms "modified avidin" and "modified streptavidin" are intended to include modifications which produce a detection signal by both direct and indirect methods.

Although not wishing to be bound to any particular technical explanation, the success of the invention is apparently due to a favorable balance of competitive binding of the non-specifically bound signaling moiety, such as a modified streptavidin or modified avidin, by the free heterologous moiety, such as free biotin, in the wash solution. The nature of the free heterologous moiety (e.g., biotin) interaction between signaling moiety (e.g. modified streptavidin) bound to detector molecules and non-specifically bound signaling moiety could not have been predicted. An important aspect of the invention, however, is the discovery that any system which utilizes streptavidin or avidin binding to biotin, or an interaction similar to that between avidin and biotin, as the mechanism for detection can benefit from this novel method of reducing background level by employing as a wash solution, designed to remove non-specifically bound signaling moiety (e.g., modified streptavidin), a composition containing free heterologous moiety (e.g., free biotin).

The following examples are provided for exemplification purposes only and are not intended to limit the scope of the invention which has been described in broad terms above.

EXAMPLE 1

This example demonstrates the reduction in the background signal upon the addition of an effective amount of biotin to a standard wash solution in a DNA assay.

Nylon membranes from two different vendors (PALL BIODYNE® nylon membrane (FIG. 1a) and MSI MAGNAGRAPH® nylon membrane (FIG. 1b)) were used in a dot blot procedure. Two membranes were chosen, one of the membranes had demonstrated a high signal to noise ratio (low background) in an initial survey of membrane types and lots, the second had demonstrated a low signal to noise ratio (high background) in the survey. Membrane strips (approximately 0.5 cm×5 cm) were prepared by soaking them for 5 minutes in water, followed by 5 minutes of soaking in a citrate buffered saline (0.3M NaCl, 0.03M sodium citrate at a pH of 7.5). Once the membranes had dried, they were gridded and numbered for identification. Biotinylated DNA was spotted onto the strips of nylon membrane with an identical series of two-fold dilutions. The dilution series ranged from 120 pg at the top of each strip to 0.85 pg at the bottom. After spotting, each strip underwent UV cross-linking, blocking for 30 minutes with a Milk Diluent Blocking (MDB) solution diluted 1:4 in water, and incubation for 20 minutes with horseradish peroxidase conjugated streptavidin (HRPSA) diluted 1:500 in diluted blocking solution (MDB). Each strip then was washed three times for 5 minutes using a standard post-HRPSA wash solution differing only in the concentration of d-biotin or of a biotin derivative.

Figure 1B:
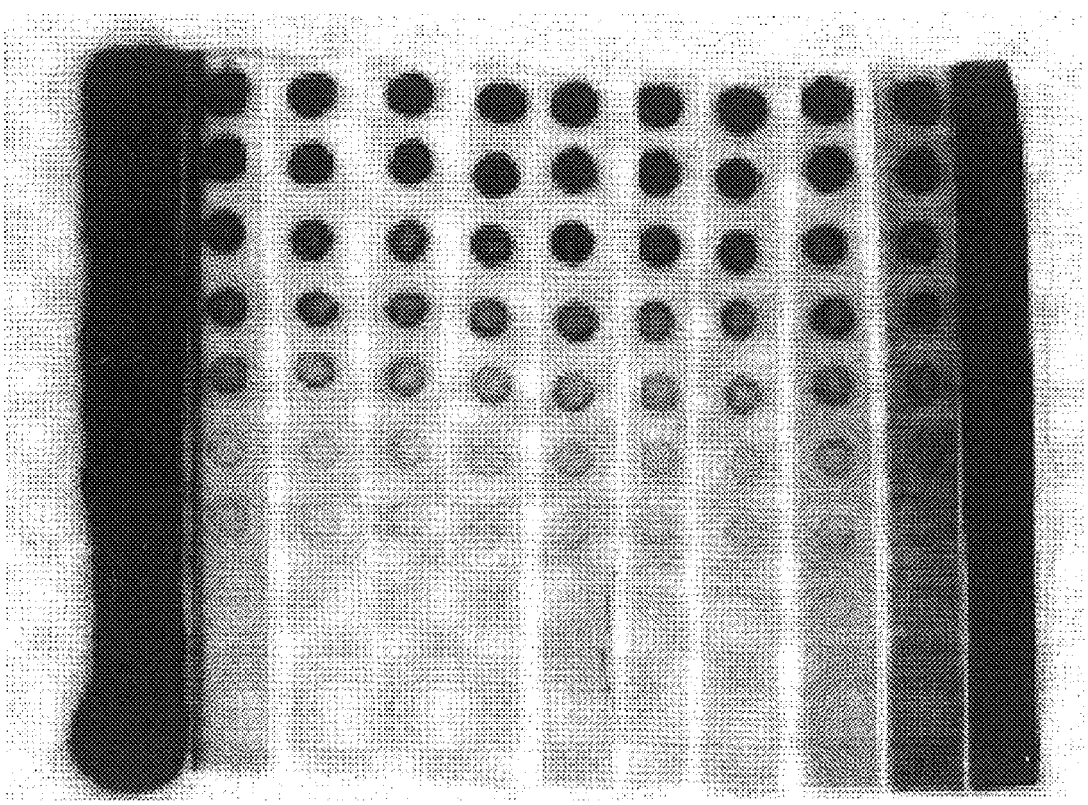

Concentrations of biotin or biotin derivative in the standard wash solution were (a) 0 µg/ml, (b) 2.5 µg/ml iminobiotin containing approximately 1% biotin, (c) 1000 ng/ml d-biotin, (d) 500 ng/ml d-biotin, (e) 250 ng/ml d-biotin, (f) 125 ng/ml d-biotin, (g) 62.5 ng/ml d-biotin, (h) 31.25 ng/ml d-biotin, (i) 15.6 ng/ml d-biotin, (j) 7.8 ng/ml d-biotin, (k) 3.9 ng/ml d-biotin. Following the wash step, the strips were incubated for 1 minute in LumiGLO® chemiluminescent substrate available from Kirkegaard & Perry Laboratories, Inc. Gaithersburg, Md. and were thereafter exposed to X-ray film for 10 minutes. FIGS. 1a and 1b are reproductions of the developed X-ray film. As shown in FIGS. 1a and 1b, a high background is observed in the series prepared without adding any biotin to the wash solution (column (a)). As one can readily appreciate on comparing column (a) to at least columns (b) through (h), gradually increasing the concentration of biotin in the wash solution enables one to decrease the level of background signal. The effective amount of biotin needed to reduce background interference in the assay for the nylon membranes from the different vendors is shown to be different in this experiment.

EXAMPLE 2

Figure 2A:
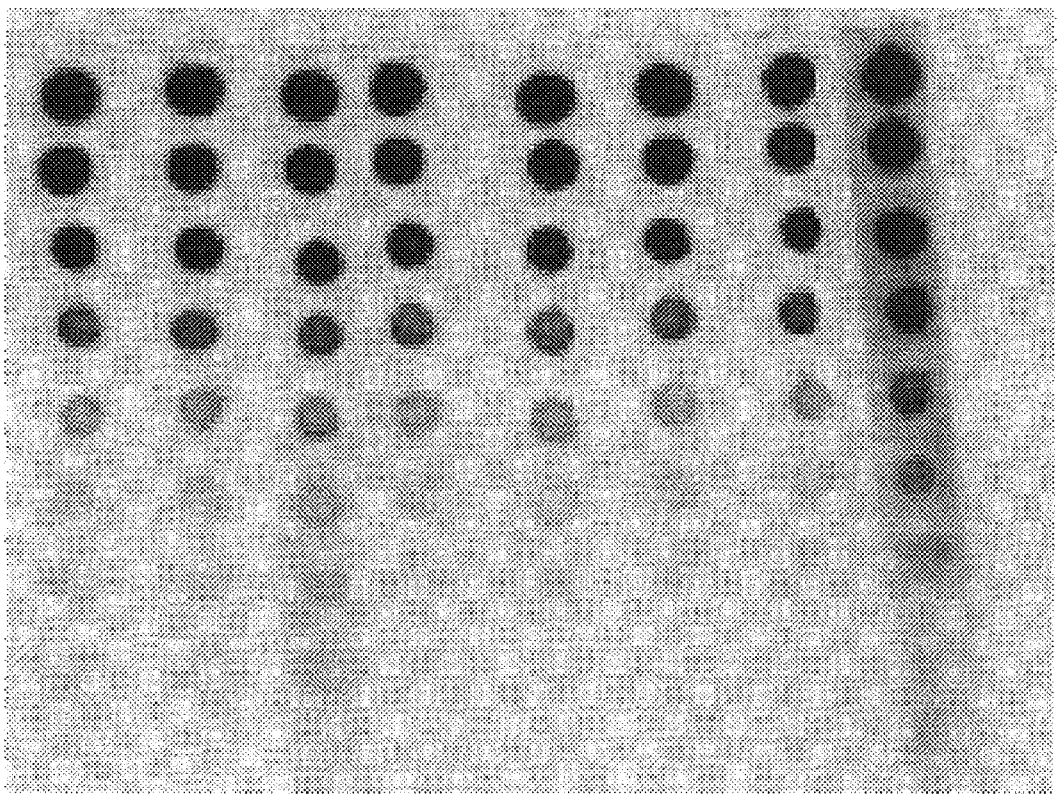
FIGS. 2*a* and 2*b* are X-ray films of a dot blot assay which show the effect of adding biotin analogs to a standard wash solution when conducting a nucleic acid assay respectively on PALL BIODYNE® (FIG. 2*a*) and MSI MAGNAGRAPH® (FIG. 2*b*) nylon membranes.
Figure 2B:
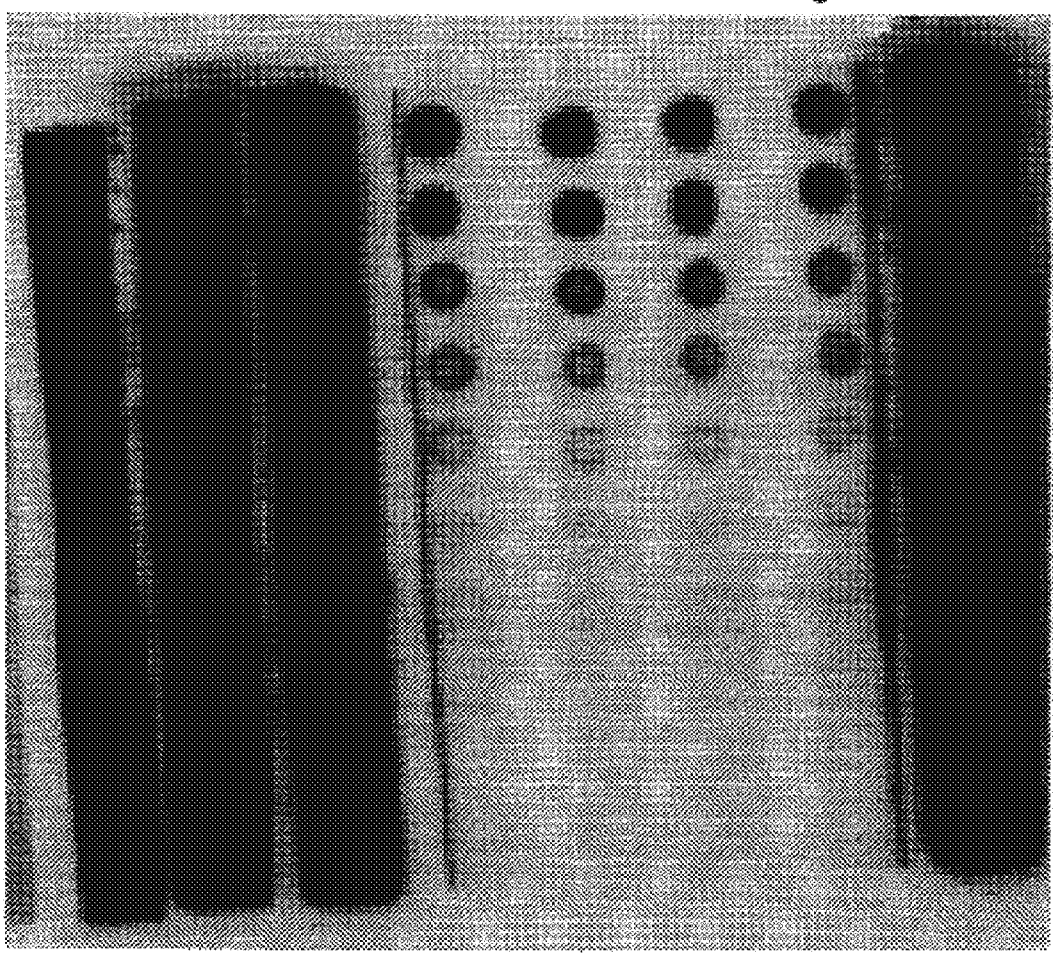

This example demonstrates that the biotin analog iminobiotin generally is not as effective as d-biotin in reducing the background signal on nylon membranes (PALL BIODYNE® nylon membrane (FIG. 2a) and MSI MAGNAGRAPH® nylon membrane (FIG. 2b).

Duplicate strips containing biotinylated DNA as prepared in Example 1 were used in this experiment. Again, each strip is an identical series of two-fold dilutions of biotinylated DNA. The dilution series ranged from 120 pg at the top of each strip to 0.85 pg at the bottom. The same procedures used in Example 1 were followed except that some of the strips were washed with a standard wash solution containing different concentrations of the biotin analog iminobiotin, instead of d-biotin. The concentrations of biotin or biotin analog, in the wash solution were as follows: (a) 40 µg/ml iminobiotin, (b) 10 µg/ml iminobiotin, (c) 2.5 µg/ml iminobiotin, (d) 5 µg/ml d-biotin, (e) 2.5 µg/ml d-biotin, (f) 1.25 µg/ml d-biotin, (g) 0.625 µg/ml d-biotin, (h) standard wash solution (i.e., no additives). FIGS. 2a and 2b are a reproduction of the X-ray film developed in accordance with the procedure used in Example 1. The figures show that including iminobiotin in the wash solution, though providing an improvement in the signal-to-noise-ratio, does not decrease the background level as well as was observed using d-biotin in the wash solution.

Comparative Example 3

Figure 3:
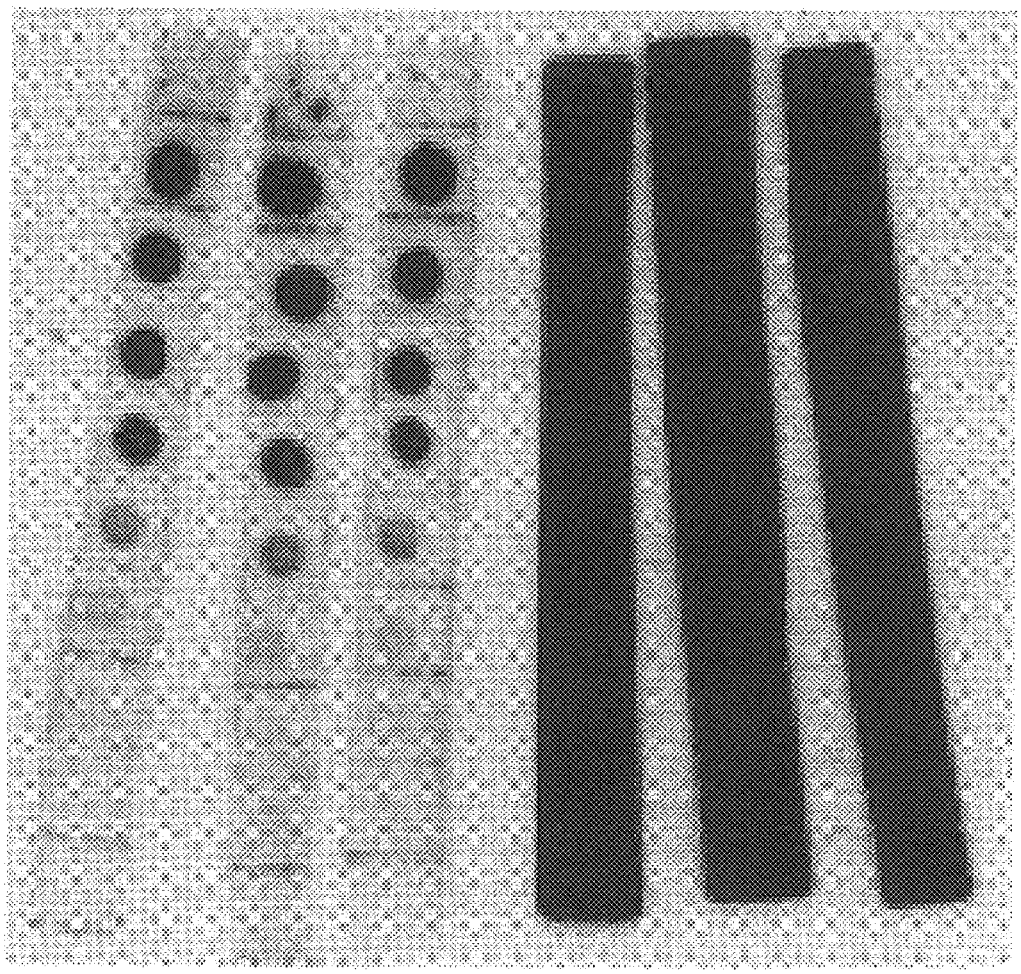
FIG. 3 is an X-ray film of a dot blot assay which shows the effect of adding urea to a standard wash solution when conducting a nucleic acid assay respectively on PALL BIODYNE® ((a), (b) and (c)) and MSI MAGNAGRAPH® ((d), (e) and (f)) nylon membranes.

This example demonstrates that adding urea to the wash solution does not have a positive effect on reducing the background signal level in the biotin-streptavidin assay conducted on nylon membranes (PALL BIODYNE® nylon membrane (FIG. 3, (a), (b) and (c) and MSI MAGNAGRAPH® nylon membrane (FIG. 3(d), (e) and (f))).

Again, duplicate strips containing a dilution series of biotinylated DNA prepared using the procedure of Example 1 were used in this example. Each strip was an identical series of two-fold dilutions of the biotinylated DNA. As before, the dilution series ranged from 120 pg at the top of each strip to 0.85 pg at the bottom. The same procedures used in Example 1 were followed, except that the strips were washed in a standard wash solution containing different concentrations of urea instead of either d-biotin or iminobiotin. Each of the strips was washed using the standard wash solution supplemented with urea as follows: (a) and (d) 0.1 M urea, (b) and (e) 0.2 M urea, (c) and (f) 0.3 M urea. As shown clearly in FIG. 3, which is a reproduction of the X-ray film of the various series developed in accordance with the procedure used in FIG. 1, none of the urea-supplemented wash solutions were effective in improving the signal-to-noise ratio to any significant extent.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

We claim:

1. In a method of detecting a target material in a sample immobilized on a solid phase support using a detector molecule, wherein the detector molecule binds to the target material, wherein said detector molecule has a heterologous moiety attached thereto, wherein said heterologous moiety attached to the detector molecule is detected by a signaling moiety, wherein the signaling moiety binds to the heterologous moiety, and wherein said method comprises a step of washing excess non-specifically bound signaling moiety with a wash solution from said solid phase support, the improvement comprising employing as said wash solution a composition comprising free heterologous moiety, wherein the heterologous moiety attached to the detector molecule is selected from the group consisting of biotin, biotin derivatives and biotin analogs; wherein the free heterologous moiety is selected from the group consisting of biotin, biotin derivatives and biotin analogs and wherein the signaling moiety is selected from the group consisting of modified streptavidin and modified avidin.

2. The method of claim 1 wherein the modified streptavidin is selected from the group consisting of streptavidin conjugated with an enzyme, streptavidin modified with a fluorophore, streptavidin modified with a colloidal moiety and streptavidin modified with a radioisotope.

3. The method of claim 2 wherein the enzyme is selected from the group consisting of horseradish peroxidase, alkaline phosphatase and beta-galactosidase.

4. The method of claim 3 wherein the detector molecule having the attached heterologous moiety is biotinylated polynucleotide.

5. The method of claim 3 wherein the detector molecule having the attached heterologous moiety is biotinylated antibody.

6. The method of claim 1 wherein the modified avidin is selected from the group consisting of avidin conjugated with an enzyme, avidin modified with a fluorophore, avidin modified with a colloidal moiety and avidin modified with a radioisotope.

7. The method of claim 6 wherein the enzyme is selected from the group consisting of horseradish peroxidase, alkaline phosphatase and beta-galactosidase.

8. The method of claim 7 wherein the detector molecule having the attached heterologous moiety is biotinylated polynucleotide.

9. The method of claim 7 wherein the detector molecule having the attached heterologous moiety is biotinylated antibody.

10. The method of claim 4 wherein the solid phase is selected from the group consisting of nylon, nitrocellulose and polyvinylidene fluoride.

* * * * *